United States Patent
Hasegawa et al.

(10) Patent No.: US 12,102,981 B2
(45) Date of Patent: Oct. 1, 2024

(54) CATALYST, METHOD FOR PREPARING CATALYST, AND METHOD FOR PRODUCING UNSATURATED CARBOXYLIC ACID AND/OR UNSATURATED CARBOXYLIC ACID ESTER

(71) Applicant: Mitsubishi Chemical Corporation, Tokyo (JP)

(72) Inventors: Toshio Hasegawa, Tokyo (JP); Norimichi Kawabe, Tokyo (JP); Akio Hayashi, Tokyo (JP); Wataru Ninomiya, Tokyo (JP); Masaya Fujisue, Tokyo (JP)

(73) Assignee: Mitsubishi Chemical Corporation, Tokyo (JP)

( * ) Notice: Subject to any disclaimer, the term of this patent is extended or adjusted under 35 U.S.C. 154(b) by 474 days.

(21) Appl. No.: 17/461,613

(22) Filed: Aug. 30, 2021

(65) Prior Publication Data

US 2021/0387165 A1 Dec. 16, 2021

Related U.S. Application Data

(63) Continuation of application No. PCT/JP2020/010570, filed on Mar. 11, 2020.

(30) Foreign Application Priority Data

Mar. 12, 2019 (JP) .................. 2019-044999

(51) Int. Cl.
| | |
|---|---|
| B01J 23/10 | (2006.01) |
| B01J 21/06 | (2006.01) |
| B01J 35/40 | (2024.01) |
| B01J 35/61 | (2024.01) |
| B01J 35/64 | (2024.01) |
| B01J 37/02 | (2006.01) |
| C07C 67/347 | (2006.01) |

(52) U.S. Cl.
CPC ............ *B01J 23/10* (2013.01); *B01J 21/066* (2013.01); *B01J 35/40* (2024.01); *B01J 35/615* (2024.01); *B01J 35/647* (2024.01); *B01J 37/0203* (2013.01); *C07C 67/347* (2013.01); *C07C 2521/06* (2013.01); *C07C 2523/10* (2013.01)

(58) Field of Classification Search
CPC . B01J 21/066; B01J 23/04; B01J 23/10; B01J 35/40; B01J 35/60; B01J 35/615; B01J 35/647; B01J 37/02; B01J 37/0203; B01J 37/0205; B01J 37/0209; B01J 37/0213; C07B 61/00; C07C 51/09; C07C 67/30; C07C 67/343; C07C 67/347; C07C 2521/06; C07C 2523/10
See application file for complete search history.

(56) References Cited

U.S. PATENT DOCUMENTS

| | | | | |
|---|---|---|---|---|
| 4,463,105 A | * | 7/1984 | Ichikawa | ............... C07C 45/49 |
| | | | | 518/716 |
| 9,782,756 B2 | | 10/2017 | Ziemian et al. | |
| 2012/0256125 A1 | | 10/2012 | Kaneyoshi et al. | |
| 2013/0018161 A1 | | 1/2013 | Ezawa et al. | |

FOREIGN PATENT DOCUMENTS

| | | |
|---|---|---|
| JP | 2002-511336 A | 4/2002 |
| JP | 2009-126846 A | 6/2009 |
| JP | 2011-224536 A | 11/2011 |
| JP | 2012-224536 A | 11/2012 |
| JP | 2015-205842 A | 11/2015 |
| RU | 2203731 C2 | 5/2003 |
| RU | 2582603 C2 | 4/2016 |
| WO | 99/52628 A1 | 10/1999 |
| WO | WO-2015163324 A1 * | 10/2015 ............. B01J 23/04 |
| WO | 2019/053438 A1 | 3/2019 |

OTHER PUBLICATIONS

Machine Translation of WO 2015/163324. (Year: 2015).*
Penrose, C. et al., 2021, Supplementary Information A simple liquid state 1H NMR measurement to directly determine the surface hydroxyl density of porous silica, Chemical Communications, 57, S1-S5. (Year: 2021).*
Office Action issued in corresponding Russian Patent Application No. 2021129523/04(062616) dated Jan. 26, 2023.
Office Action issued in counterpart Korean Patent Application No. 10-2021-7032042 dated May 30, 2023.

(Continued)

*Primary Examiner* — Brian A McCaig
(74) *Attorney, Agent, or Firm* — Morgan, Lewis & Bockius LLP

(57) ABSTRACT

The present invention is a catalyst comprising:
(i) a compound comprising at least one first metal element selected from boron, magnesium, zirconium, and hafnium, and
(ii) an alkali metal element,
wherein the compound and the alkali metal element are supported on a carrier having silanol groups,
an average particle size of the compound of the first metal element is 0.4 nm or more and 50 nm or less,
the catalyst satisfies the following formula (1):

$$0.90 \times 10^{-21} (\text{g/number}) \leq X/(Y \times Z) < 10.8 \times 10^{-21} (\text{g/number}) \quad \text{formula (1)},$$

in which X is a molar ratio of the alkali metal element to the at least one first metal element in the catalyst, Y is a BET specific surface area of the catalyst ($m^2/g$), and Z is a number of the silanol groups per unit area (number/$nm^2$).

19 Claims, No Drawings

(56) References Cited

OTHER PUBLICATIONS

Office Action issued in counterpart Taiwanese Patent Application No. 109108074 dated Oct. 2, 2023.
Extended European Search Report issued in counterpart European Patent Application No. 20770376.0 dated May 11, 2022.
International Search Report issued in related International Patent Application No. PCT/JP2020/010570 dated May 19, 2020.
Office Action issued in counterpart Iranian Patent Application No. 140050140030004281 dated Oct. 29, 2023.
Office Action issued in counterpart Singapore Patent Application No. 11202109990X dated Aug. 4, 2022.
Office Action issued in counterpart Canadian Patent Application No. 3130565 dated Aug. 12, 2022.
Office Action issued in counterpart Indonesian Patent Application No. P00202108071 dated Aug. 10, 2022.
Office Action issued in corresponding Russian Patent Application No. 2021129523/04(062616) dated Apr. 4, 2022.
Search Report issued in corresponding Russian Patent Application No. 2021129523/04(062616) dated Apr. 4, 2022.
Office Action issued in corresponding Japanese Patent Application No. 2021-505105 dated May 22, 2022.
Office Action issued in counterpart Chinese Patent Application No. 202080019963.X dated Feb. 13, 2023.
Office Action issued in corresponding Indian Patent Application No. 202147045128 dated Dec. 14, 2023.
Office Action issued in counterpart Brazilian Patent Application No. BR112021016346-8 dated Dec. 12, 2023.
Office Action issued in Saudi Patent Application No. 521430274 dated Mar. 21, 2024.

\* cited by examiner

CATALYST, METHOD FOR PREPARING CATALYST, AND METHOD FOR PRODUCING UNSATURATED CARBOXYLIC ACID AND/OR UNSATURATED CARBOXYLIC ACID ESTER

TECHNICAL FIELD

The present invention relates to a catalyst, a method for producing a catalyst, and a method for producing an unsaturated carboxylic acid and/or an unsaturated carboxylic acid ester.

BACKGROUND TECHNIQUES

Methyl methacrylate is used in a variety of applications. As for methyl methacrylate, a large number of production methods such as an ACH method and a direct oxidation method using a C4 raw material have been studied, but in recent years, a production method called an Alpha technology has attracted attention.

In general, an Alpha technology is a method for producing methyl methacrylate by producing methyl propionate using ethylene as a raw material as a pre-stage reaction and performing an aldol condensation reaction of the methyl propionate as a post-stage reaction, and various catalysts have been studied in order to improve selectivity and yield of methyl methacrylate in a post-stage reaction in particular.

For example, Patent Document 1 proposes to use a catalyst containing a porous high surface area silica containing 1 to 10% by mass of an alkali metal and containing a specific amount of a compound of at least one modifier element selected from boron, magnesium, aluminum, zirconium and hafnium as a catalyst for a post-stage reaction in an Alpha technology.

PRIOR-ART DOCUMENT

Patent Document

Patent Document 1: JP2002-511336

SUMMARY OF THE INVENTION

Problems to be Solved by the Present Invention

In order to produce methyl methacrylate, which is a target compound, in such an industrial process with high productivity, it is desired to produce the target product in high selectivity and high yield.

However, it has been found that, even when the catalyst described in Patent Document 1 is used, there is a possibility that the selectivity of methyl methacrylate is not sufficient.

Means for Solving the Problems

In view of the above circumstances, the present invention has been made, and the present inventors have found that the above problem can be solved by using a specific catalyst, and has reached the present invention.

That is to say, the gist of the invention is as follows.

[1] A catalyst comprising:
(i) a compound comprising at least one first metal element selected from boron, magnesium, zirconium, and hafnium, and
(ii) an alkali metal element,
wherein the compound and the alkali metal element are supported on a carrier having silanol groups,
an average particle size of the compound of the first metal element is 0.4 nm or more and 50 nm or less,
the catalyst satisfies the following formula (1):

$$0.90 \times 10^{-21} (\text{g/number}) \leq X/(Y \times Z) < 10.8 \times 10^{-21} (\text{g/number}) \quad \text{formula (1)},$$

in which X is a molar ratio of the alkali metal element to the at least one first metal element in the catalyst, Y is a BET specific surface area of the catalyst ($m^2/g$), and Z is a number of the silanol groups per unit area (number/$nm^2$).

[2] The catalyst according to [1], wherein the molar ratio X of the alkali metal element to the first metal element is 1.3 or more and 6.0 or less.

[3] The catalyst according to [1] or [2], wherein the alkali metal element comprises cesium.

[4] The catalyst of any one of [1] to [3], wherein the first metal element comprises zirconium.

[5] The catalyst according to any one of [1] to [4], which is a catalyst for producing an unsaturated carboxylic acid and/or an unsaturated carboxylic ester.

[6] A method for producing an unsaturated carboxylic acid and/or an unsaturated carboxylic acid ester by reacting a carboxylic acid and/or a carboxylic acid ester with formaldehyde in the presence of the catalyst according to any one of [1] to [5].

[7] A method for producing a catalyst comprising (i) a compound comprising at least one first metal element selected from boron, magnesium, zirconium, and hafnium, and (ii) an alkali metal element the compound and the alkali metal element being supported on a carrier, the method comprising impregnating the carrier with a solution or dispersion containing an inorganic salt of the first metal element to obtain the first solid, and impregnating the first solid with a solution or dispersion containing an alkali metal salt to obtain the second solid.

wherein an average particle size of a compound of the first metal element is 0.4 nm or more and 50 nm or less, and the catalyst satisfies the following formula (2):

$$1.5 \times 10^{-21} (\text{g/number}) \leq X'/(Y' \times Z') \leq 17.0 \times 10^{-21} (\text{g/number}) \quad \text{formula}(2),$$

in which X' is a molar ratio of the alkali metal element to the at least one first metal element in the catalyst, Y' is a BET specific surface area of the catalyst ($m^2/g$), and Z' is a number of the silanol groups per unit area (number/$nm^2$).

[8] The method according to [7], wherein a solvent of the solution or dispersion containing an inorganic salt of the first metal element contains alcohol.

[9] The method according to [7] or [8], wherein the first metal element is zirconium.

[10] The method according to any one of [7] to [9], wherein the alkali metal element is cesium.

Effect of Invention

According to the present invention, it is possible to obtain a catalyst capable of producing an unsaturated carboxylic acid and/or an unsaturated carboxylic acid ester at a high selectivity in the reaction of a carboxylic acid and/or a carboxylic acid ester and a formaldehyde, and a method for producing the catalyst.

Further, it is possible to provide a method for producing a carboxylic acid and/or an unsaturated carboxylic acid with high selectivity.

DETAILED DESCRIPTION OF THE PRESENT INVENTION

Hereinafter, as an embodiment of the present invention, a method for producing an unsaturated carboxylic acid and/or an unsaturated carboxylic acid ester by an aldol condensation reaction of a carboxylic acid and/or a carboxylic acid ester and a formaldehyde in the presence of a catalyst will be described.

<Catalyst>

The catalyst according to the present embodiment has a configuration in which at least one first metal element selected from boron, magnesium, zirconium and hafnium and an alkali metal element are supported on a carrier having silanol groups, and an average particle size of a compound containing the first metal element is 0.4 nm or more and 50 nm or less, and when a molar ratio of the alkali metal element to the first metal element is X, a BET specific surface area ($m^2/g$) of the catalyst is Y, and a number of silanol groups per unit area (number/$nm^2$) of the catalyst is Z, the following formula (1) is satisfied.

$$0.90 \times 10^{-21} (\text{g/number}) \leq X/(Y \times Z) < 10.8 \times 10^{-21} (\text{g/number}) \quad \text{formula (1)}$$

The molar number of the alkali metal element used in formula (1) shall mean the molar number of all alkali metal elements contained in the catalyst.

In other words, when 2 or more kinds of alkali metal elements are used, it is assumed to mean the total number of moles of 2 or more kinds of alkali metal elements.

Similarly, the molar number of the first metal element is also intended to mean the total number of moles of the 2 or more first metal elements when 2 or more first metal elements are used.

In addition, in the above formula (1), the molar ratio of the alkali metal element to the first metal element, the number of the silanol groups on the surface of the carrier, and the BET specific surface area can be calculated by the method described in the examples described later, respectively.

The mechanism by which the above formula (1) can be satisfied to produce unsaturated carboxylic acids and/or unsaturated carboxylic esters with high selectivity in the reaction of carboxylic acids and/or carboxylic esters with formaldehyde is not clear, but by satisfying the above formula (1), the first metal element and the alkali metal element are moderately highly dispersed on the catalyst surface, and it is believed that the selectivity of unsaturated carboxylic acids and/or unsaturated carboxylic esters can be improved due to the high dispersion.

The alkali metal element, which is a catalyst component, is preferably lithium, sodium, potassium, cesium or rubidium, among them, potassium, rubidium or cesium is more preferred, and particularly preferably cesium. Note that 1 kinds of alkali metal elements may be used, or 2 or more kinds thereof may be used.

The first metal element is selected from boron, magnesium, zirconium and hafnium as described above, among them, boron or zirconium is preferred, and zirconium is particularly preferred. Note that 1 kinds of these metal elements may be used, or 2 or more kinds thereof may be used.

Among the above formula (1), the value of $X/(Y \times Z)$ is further preferred to be $1.0 \times 10^{-21}$ (g/number) or more for yield improvement of the product, and is particularly preferred to be $1.5 \times 10^{-21}$ (g/number) or more, while it is even more preferred to be $10.7 \times 10^{-21}$ (g/number) or less and to be $10.5 \times 10^{-21}$ (g/number) or less for yield reduction inhibition of the product.

The average particle size of the compound containing the first metal element constituting the catalyst is among the above, preferably 0.5 nm or more, particularly preferably 0.8 nm or more, whereas, preferably 30 nm or less, more preferably 20 nm or less, more preferably 10 nm or less, further preferably 8 nm or less, more preferably 6 nm or less, further preferably 5 nm or less, particularly preferably 4 nm or less, particularly preferably 3 nm or less.

Although there is no particular limitation as long as the above formula (1) is satisfied, the molar ratio X of the alkali metal element to the first metal element is preferably 1.3 or more, more preferably 1.5 or more, still more preferably 1.7 or more, and particularly preferably 1.9 or more, for the purpose of improving the yield of the target product, and on the other hand, it is preferably 6.0 or less, more preferably 5.5 or less, and particularly preferably 5.0 or less, for the purpose of suppressing the yield decrease of the target product.

The amount of the alkali metal element to the total mass of the catalyst component and the carrier is not particularly limited as long as the above formula (1) is satisfied, but is preferably 4% by mass or more, more preferably 7% by mass or more, and particularly preferably 9% by mass or more, in order to improve the yield of the target product, and on the other hand, is preferably 25% by mass or less, more preferably 18% by mass or less, and particularly preferably 14% by mass or less, in order to suppress the decrease in the yield of the target product.

The amount of the first metal element to the total mass of the catalyst component and the carrier is not specifically restricted as long as the above formula (1) is met, but it is preferable to be 0.3% or more by mass, to be 0.5% or more by mass, and is particularly preferable to be 1.0% or more by mass, in order to improve the yield of the target product, while it is preferable to be 10% or less by mass, to be 6% or less by mass, and to be 5% or less by mass, to be 4% or less by mass, in order to reduce the yield of the product The catalyst component supported on the carrier may contain a metal element other than the above.

Examples thereof include aluminum, titanium, and iron.

In addition, the ratio of the element to the total mass of the catalyst component supported on the carrier is preferably 1.0% by mass or less, more preferably 0.5% by mass or less, and particularly preferably 0.2% by mass or less, in order to suppress the yield decrease of the target.

The catalyst component supported on the carrier may be constituted by including other elements in addition to the above-mentioned metal elements.

For example, it may be configured to include an element derived from production of a catalyst component.

The carrier is capable of supporting a catalyst component, and there is no particular limitation as long as it has silanol groups on its surface, but specifically, it is preferably a porous inorganic compound carrier containing silicon oxide.

The material constituting the carrier is not particularly limited, and examples thereof include silica, silica alumina, zeolite, titania containing silica, or zirconia containing silica.

Of these, silica is preferred.

Incidentally, the carrier can be used commercially available.

Examples include trade name: CARiACT (manufactured by Fuji Silysia Chemical Co., Ltd.), etc.

The number Z of silanol groups per unit area of catalysis is not specifically restricted as long as it meets the above formula (1), but it is preferable to be 0.5 number/nm$^2$ or more, to be 0.8 number/nm$^2$ or more, to be 2.5 number/nm$^2$ or more, and is particularly preferable to be 4 number/nm$^2$ or more, in order to improve the yield of the target product, and on the other hand, is preferable to be 20 number/nm$^2$ or less, to be 17 number/nm$^2$ or less, and to be 15 number/nm$^2$ or less, to be particularly preferable to be 13 number/nm$^2$ or less in order to suppress the yield decrease of the target.

Although there is no particular limitation as long as the BET specific surface area Y of the catalyst satisfies the above formula (1), it is preferably 50 m$^2$/g or more, more preferably 70 m$^2$/g or more, still more preferably 90 m$^2$/g or more, particularly preferably 100 m$^2$/g or more, and is preferably 600 m$^2$/g or less, still more preferably 500 m$^2$/g or less, particularly preferably 350 m$^2$/g or less, in order to improve the yield of the target.

There is no particular limitation on the shape of the carrier, and examples thereof include powdery, granular, pelletized, or tableted.

Although there is no particular limitation on the average particle size of the carrier, it is preferably 500 μm or more, more preferably 1 mm or more, and particularly preferably 1.5 mm or more, for suppressing pressure loss and suppressing by-products during the reaction, and on the other hand, it is preferably 10 mm or less, more preferably 6 mm or less, and particularly preferably 5 mm or less for suppressing by-products.

Although there is no particular limitation on the average pore diameter possessed by the carrier, it is preferably 3 nm or more, more preferably 5 nm or more, and particularly preferably 10 nm or more, for the purpose of suppressing by-products, and on the other hand, it is preferably 200 nm or less, more preferably 150 nm or less, and particularly preferably 100 nm or less, in order to ensure a specific surface area.

The shape of the catalyst is not specifically restricted and may include spherical, columnar or ring shapes.

Note that the average volume of the catalyst is not particularly limited, but is preferably 0.06 mm$^3$ or more and 550 mm$^3$ or less.

The method for producing a catalyst is not particularly limited and can be produced by supporting a metal element on a carrier.

However, from the viewpoint of preventing deterioration of the catalyst, it is preferable to produce the catalyst by the method having at least a step of impregnating the carrier with an average particle size of an inorganic salt of a first metal element in a solution or dispersion in a state of 0.4 nm or more and 50 nm or less.

Hereinafter, an example is shown in which a catalyst is produced by the following first step to 4th step as a preferred form.

First step: the step of dissolving or dispersing an inorganic salt of the first metal element in the first solvent to obtain a solution or dispersion.

Second step: the step of impregnating the carrier with the solution or dispersion obtained by the first step to obtain the first solid content.

Third step: the step of dissolving or dispersing an alkali metal salt in the second solvent to obtain a solution or dispersion.

Fourth step: the step of mixing the first solid content obtained by the second step with the solution or dispersion liquid obtained by the third step to obtain the second solid content.

Each step is described in detail below.

<First Step>

The first metal element constituting the inorganic salt of the first metal element includes the first metal element described above.

The inorganic salt of the first metal element is an inorganic compound containing no hydrocarbon, and there is no particular limitation, and for example, a carbonate, a nitrate, a sulfate, an acetate, an ammonium salt, an oxide or a halide of the first metal element can be used alone or in combination.

For example, when the first metal element is zirconium, examples thereof include zirconium oxynitrate, zirconium sulfate, zirconium carbonate, zirconium perchlorate, and zirconium acetate.

When the first metal element is boron, examples thereof include boron oxide and the like.

When the first metal element is magnesium, examples thereof include magnesium nitrate, magnesium sulfate, magnesium carbonate, and magnesium acetate.

When the first metal element is hafnium, examples thereof include hafnium nitrate, hafnium sulfate, hafnium perchlorate, and hafnium acetate.

The first solvent is not particularly limited and includes water or an organic solvent.

Among them, an alcohol is more preferred as an organic solvent in order to improve dispersibility of an inorganic salt of a first metal element.

As the alcohol, an alcohol having 1 or more and 6 or less carbon atoms is preferred, and methanol is particularly preferred.

Although there is no particular limitation on the amount of the inorganic salt of the first metal element with respect to 100 ml of the solvent, in order to support the desired first metal element, it is preferably 2 mmol or more, more preferably 5 mmol or more, and particularly preferably 10 mmol or more, and on the other hand, it is preferably 60 mmol or less, more preferably 50 mmol or less, and particularly preferably 40 mmol or less, in order to suppress the supported amount.

In addition, when the inorganic salt of the first metal element is dissolved or dispersed in the first solvent, the first solvent may be stirred.

In addition, it is preferable that the obtained solution or dispersion is left to stand.

There is no particular limitation on the standing time, but if the standing time is long, the average particle size of the inorganic salt of the first metal element in the solution or dispersion tends to be small.

In particular, in the present invention, as will be described later, when a solution or a dispersion is impregnated into a carrier in the second step, it is preferable to have a specific average particle size, and therefore, it is preferable to keep it still until a desired particle size is obtained.

Specifically, the standing time is preferably 30 minutes or more, more preferably 2 hours or more, still more preferably 4 hours or more, and particularly preferably 16 hours or more.

On the other hand, it is preferably 100 hours or less, more preferably 80 hours or less, and particularly preferably 50 hours or less.

<Second Step>

The carrier can use the carrier described above.

The method of impregnating the carrier with the first solvent is not particularly limited and can be used by a known method.

For example, there may be a pore-filling method using a first solvent satisfying a pore volume of a carrier, a soaking method in which a carrier is immersed in a first solvent, and the like.

Although there is no particular limitation on the amount of the carrier to the first solvent, in order to uniformly support the first metal element, the ratio of the first solvent to the carrier is preferably 0.9 times or more of the pore volume of the carrier, and on the other hand, for the purpose of reducing the amount of the solvent used, it is preferably 10 times or less, particularly preferably 5 times or less, of the pore volume of the carrier.

The average particle size of the inorganic salt of the first metal element when the carrier is impregnated with the first solvent in which the inorganic salt of the first metal element is dispersed, in order to obtain a good catalytic property, as described above, it is preferred to be 50 nm or less, it is even more favorable to be 30 nm or less, it is more favorable to be 20 nm or less, it is even more favorable to be 10 nm or less, more favorable to be 5 nm or less, further favorable to be 3 nm or less, particularly favorable to be 2 nm or less.

On the other hand, even if the average particle size of the inorganic salt of the first metal element is too small, since the change in the selectivity of the target product at the time of the reaction is extremely small, when both the selectivity of the target product and the productivity of the catalyst are considered, the average particle size of the inorganic salt of the first metal element is preferably 0.4 nm or more, more preferably 0.5 nm or more, and particularly preferably 0.8 nm or more.

Mean particle size of inorganic salt is obtained by measuring 0.1 mol/l inorganic salt solution using a laser light at a wavelength of 633 nm by dynamic light scattering, and calculating the volume distribution.

The reason why the selectivity of the target product is improved when the average particle size of the inorganic salt of the first metal element is in the above range is not clear, but this may be that the first metal element has high dispersibility on the carrier when the catalyst is produced by this method.

Although there is no particular limitation on the impregnation time of the carrier, it is preferable that the impregnation time is 15 minutes or more and 50 hours or less in order to support the first metal element.

In obtaining the first solid content, it is preferable to remove the first solvent.

The removal of the first solvent can be carried out by a known method.

For example, the first solvent can be removed using a rotary evaporator.

Further, for example, the first solvent can be removed by separating the solid matter and the first solvent by filtration.

Further, it is preferable that the obtained first solid content is dried or calcined, but it is not necessarily necessary to perform.

By drying or calcination, the first solvent remaining in the first solid content can be removed.

These heating temperatures are preferably 50° C. or more, more preferably 70° C. or more, still more preferably 120° C. or more, particularly preferably 400° C. or more, while 800° C. or less is preferred, more preferably 700° C. or less, and particularly preferably 600° C. or less.

Although there is no particular limitation on the heating time, among the above, particularly when the heating temperature is 400° C. or more and 800° C. or less, it is preferably 15 minutes or more, more preferably 30 minutes or more, particularly preferably 1 hours or more, and on the other hand, is preferably 100 hours or less, particularly preferably 50 hours or less.

By the process mentioned above, the first metal element will be present in the state of the compound, the average particulate diameter of the compound consisting of the first metal element, in order to obtain a good catalyst property, it is preferred to be 50 nm or less, it is even more favorable to be 30 nm or less, it is more favorable to be 20 nm or less, it is even more favorable to be 10 nm or less, it is even more favorable to be 8 nm or less, it is more favorable to be 6 nm or less, it is even more favorable to be 5 nm or less, it is even more favorable to be 4 nm or less, and it is particularly favorable to be 3 nm or less.

On the other hand, even if the average particle size of the compound composed of the first metal element is too small, since the change in the selectivity and the yield of the target product at the time of the reaction is extremely small, when both the selectivity of the target product and the productivity of the catalyst are considered, the average particle size of the compound composed of the first metal element is more preferably 0.4 nm or more, still more preferably 0.5 nm or more, and particularly preferably 0.8 nm or more.

The average particle size of the compound composed of the first metal element can be calculated from an image obtained by observing a flake having a solid content of 300 nm or less using a transmission electron microscope.

Note that, although the specific composition of the compound composed of the first metal element is not clear, an inorganic salt of the first metal element, an oxide of the first metal element, a composite oxide of the carrier and the first metal element, and the like are considered.

Although the reason why the deterioration of the catalyst is suppressed by the average particle size of the compound inorganic salt composed of the first metal element being within the above range is not clear, it is considered that the first metal element has high dispersibility on the carrier.

Since the values of the BET specific surface area Y and the number of silanol groups Z of the carrier tend to change during the production of the catalyst, in order to produce a catalyst which improves the selectivity of the unsaturated carboxylic acid and/or the unsaturated carboxylic ester in the reaction of the carboxylic acid and/or the carboxylic ester and the formaldehyde, the molar ratio of the alkali metal element to the first metal element is X', and in the second step, when the BET specific surface area of the carrier when the carrier is impregnated into the solution or the dispersion obtained by the first step is Y' ($m^2/g$) and the number of silanol groups per unit area of the carrier is Z' (number/$nm^2$), it is preferable to satisfy the following formula (2).

$$1.5 \times 10^{-21} (g/number) \leq X'/(Y' \times Z') \leq 17.0 \times 10^{-21} (g/number) \quad \text{formula (2)}$$

Note that the molar ratio X' of the alkali metal element to the first metal element used at the time of producing the catalyst is usually the same value as X in the above formula (1).

In the above formula (2), the value of $X'/(Y' \times Z')$ is more preferably $2.0 \times 10^{-21}$ (g/number) or more, particularly preferably $2.3 \times 10^{-21}$ (g/number) or more, in order to improve the yield of the product, and further preferably $15.0 \times 10^{-21}$ (g/number) or less, and particularly preferably $10.0 \times 10^{-21}$ (g/number) or less, in order to suppress the reduction in the yield of the product.

The BET specific surface area Y' ($m^2/g$) of the carrier of the carrier when the solution or dispersion containing the first metal element is impregnated into the carrier is not particularly limited as long as it satisfies the above formula (1), it is preferable to have 50 m²/g or more, more preferably 60 m²/g or more, more preferably 70 m²/g or more, more preferably 90 m²/g or more, and particularly preferably 100 m²/g or more, in order to improve the yield of the target product. On the other hand, it is preferable to have 600 m²/g or less, more preferably 500 m²/g or less, and still more preferably 350 m²/g or less 300 m²/g or less is particularly preferred.

The number $Z'$ (number/nm²) of silanol groups per unit area of the carrier surface of the carrier when the solution or dispersion containing the first metal element is impregnated into the carrier is not particularly limited as long as the above formula (2) is satisfied, but it is preferable to have 0.5 number/nm² or more, more preferably 0.8 number/nm² or more, more preferably 2.5 number/nm² or more, and particularly preferably 4 number/nm² or more, in order to improve the yield of the target product. On the other hand, it is preferable to have 15 number/nm² or less, more preferably 13 number/nm² or less, and 11 number/nm² or less is particularly preferred, in order to suppress the reduction in the yield of the product.

Note that, except for $X'$, $Y'$ and $Z'$, it may be appropriately adjusted so as to obtain a desired catalyst.

<Third Step>

The alkali metal element includes the alkali metal element described above.

The alkali metal salt is not particularly limited, and a carbonate, a nitrate, a sulfate, an acetate, an ammonium salt, an oxide, a halide, or the like of an alkali metal element can be used alone or in combination.

For example, when the alkali metal element is cesium, examples thereof include cesium carbonate, cesium bicarbonate, cesium nitrate, and cesium sulfate.

When the alkali metal element is lithium, lithium carbonate, lithium nitrate, and the like may be mentioned.

When the alkali metal element is sodium, examples thereof include sodium carbonate, sodium nitrate, and sodium sulfate.

When the alkali metal element is potassium, examples thereof include Potassium Carbonate, Potassium Nitrate, and Potassium Sulfate.

When the alkali metal element is rubidium, rubidium carbonate, rubidium nitrate, rubidium sulfate, and the like may be mentioned.

The second solvent is not particularly limited and includes water or organic solvents.

Among them, an alcohol is preferred as an organic solvent in order to improve dispersibility of an alkali metal salt.

As the alcohol, an alcohol having 1 or more and 6 or less carbon atoms is preferred, and methanol is particularly preferred.

Although there is no particular limitation on the amount of the alkali metal salt to 100 ml of the solvent, it is preferably 6 mmol or more, more preferably 14 mmol or more, and particularly preferably 25 mmol or more, for the purpose of improving the yield of the product, and on the other hand, it is preferably not more than 60 mmol, more preferably 50 mmol or less, and particularly preferably 40 mmol or less in order to suppress the yield decrease of the product.

In addition, when the alkali metal salt is dissolved or dispersed in the second solvent, the second solvent may be stirred.

In addition, it is preferable that the obtained solution or dispersion is left to stand.

There is no particular limitation on the standing time, but if the standing time is long, the average particle size of the alkali metal salt in the solution or dispersion tends to be small.

Specifically, the standing time is preferably 15 minutes or more, and preferably 50 hours or less.

Note that the third step may be performed before the second step or after the second step.

<The Fourth Step>

Although there is no particular limitation on the method of mixing the first solid content obtained by the second step with the solution or dispersion liquid obtained by the third step, it is preferable to impregnate the first solid content obtained by the second step into the solution or dispersion liquid obtained by the third step.

The method of impregnating the carrier with the second solvent is not particularly limited and can be used by a known method.

For example, there may be a pore-filling method using the second solvent that fills the pore volume of the carrier, or an immersion method in which the carrier is immersed in the second solvent.

Although there is no particular limitation on the first solid content to the solution or dispersion, it is preferable that the ratio of the solution or dispersion to the first solid content is 0.9 times or more of the pore volume of the carrier in order to uniformly support the alkali metal, while it is preferably 10 times or less, particularly preferably 5 times or less, of the pore volume of the carrier in order to reduce the amount of the solvent used.

Although there is no particular limitation on the impregnation time, it is preferably 15 minutes or more, more preferably 1 hours or more, for the purpose of supporting the alkali metal, and on the other hand, it is preferably 50 hours or less, and still more preferably 30 hours or less, for the purpose of improving the productivity of the catalyst.

In obtaining the second solid content, is preferable to remove the second solvent.

Removal of the second solvent can be carried out by a known method.

For example, a rotary evaporator may be used to remove the second solvent.

Further, for example, the second solvent can be removed by filtration.

Further, although not essential, it is preferable that the obtained second solid content is dried or calcined.

By drying or calcination, the second solvent remaining in the second solid can be removed.

These heating temperatures are preferably 50° C. or more, more preferably 70° C. or more, still more preferably 120° C. or more, particularly preferably 400° C. or more, while 800° C. or less is preferred, more preferably 700° C. or less, and particularly preferably 600° C. or less.

Among the above, particularly when the heating temperature is 400° C. or more and 800° C. or less, it is preferably 15 minutes or more, more preferably 30 minutes or more, particularly preferably 1 hours or more, and is preferably 100 hours or less, particularly preferably 50 hours or less.

The second solid content thus produced can be used as a catalyst.

Carriers generally tend to be highly hygroscopic.

Therefore, it is preferable that the carrier is calcined to remove moisture before the catalyst component is supported.

Further, it is preferable that the carrier baked in advance is stored in an environment in which moisture is removed.

In other words, it is preferable that the carrier is stored in a desiccator, dry air, or dry inert gas, but these techniques do not necessarily have to be used.

The molar ratio of the alkali metal element and the first metal element supported on the carrier can be adjusted by adjusting the amount of preparation.

There is no particular limitation on the method of adjusting the number of silanol groups per unit area of the carrier surface.

For example, if the silicon oxide content in the carrier is increased, the number of silanol groups on the surface of the carrier tends to increase, and if the silicon oxide content in the carrier is reduced, the number of silanol groups on the surface of the carrier tends to decrease.

Further, although there is no particular limitation on the method of adjusting the BET specific surface area of the carrier, if the pore ratio of the carrier is increased, the BET specific surface area of the carrier tends to increase, and if the pore ratio of the carrier is reduced, the BET specific surface area of the carrier tends to decrease.

Therefore, it is only necessary to use a carrier having pores such that a desired BET specific surface area is obtained.

In other words, in producing a catalyst that satisfies the above formula (1), the molar ratio of the alkali metal element to the first metal element, the number of silanol groups per unit area of the support surface, and the BET specific surface area of the support should each be adjusted as described above.

In the presence of the catalyst produced according to this embodiment, an unsaturated carboxylic acid and/or an unsaturated carboxylic acid ester can be produced by reacting a carboxylic acid and/or a carboxylic acid ester with formaldehyde.

In other words, using a carboxylic acid and/or a carboxylic acid ester as a raw material, an unsaturated carboxylic acid and/or an unsaturated carboxylic acid ester corresponding to these carboxylic acids and/or carboxylic acid esters can be produced.

The unsaturated carboxylic acid and/or the unsaturated carboxylic acid ester is preferably one represented by the following formula.

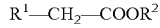

$$R^1—CH_2—COOR^2$$

In the above formula, $R^1$ and $R^2$ each independently represents a hydrogen atom or an alkyl group having 1 or more and 12 or less carbon atoms.

Among them, the catalyst according to the present embodiment is particularly effective in a method for producing methacrylic acid and/or methyl methacrylate by reaction of methyl propionate with formaldehyde.

The molar ratio of formaldehyde to the total number of moles of the carboxylic acid and the carboxylic ester used in the reaction of the carboxylic acid and/or the carboxylic acid ester with formaldehyde is not particularly limited, but is preferably in the range of 0.05 or more and 20 or less, and more preferably in the range of 0.2 or more and 15 or less, in order to improve the yield of the target product.

In addition, it is preferable that the above reaction is further carried out in the presence of an alcohol in order to suppress hydrolysis of the ester.

In the above reaction, when an alcohol is used, the molar ratio of the alcohol to the total number of moles of the carboxylic acid and/or the carboxylic acid ester is not particularly limited, but is preferably in a range of 0.05 or more and 20 or less, and more preferably in a range of 0.1 or more and 10 or less.

In addition, a compound other than the above may be contained within a range not significantly impairing the effect of the present invention. For example, it may contain water.

Although there is no particular limitation on the reaction temperature in the above reaction, in order to improve the yield of the target product, it is preferably 100° C. or more, more preferably 200° C. or more, and particularly preferably 250° C. or more, and on the other hand, it is preferably 400° C. or less, more preferably 370° C. or less, and particularly preferably 360° C. or less, in order to suppress the yield decrease of the target product.

Although there is no particular limitation on the contact time in the above reaction, it is preferably 0.1 seconds or more, still more preferably 1 seconds or more, and particularly preferably 2 seconds or more, for the purpose of improving the yield of the target product, and on the other hand, it is preferably 100 seconds or less, more preferably 50 seconds or less, and particularly preferably 30 seconds or less, for suppressing by-products.

There is no particular limitation on the method for producing the carboxylic acid and/or the alkanoic ester serving as a raw material of the above reaction, and can be produced by a known method.

For example, in the case of methyl propionate, it is preferably produced by a carbonylation reaction of ethylene.

Hereinafter, a reaction by carbonylation of ethylene will be described.

The reaction is a method for producing methyl propionate by reacting ethylene with carbon monoxide in the presence of a catalyst.

The amount of ethylene to carbon monoxide is not particularly limited, but is preferably 0.01 mol % or more, more preferably 0.1 mol % or more, and on the other hand, is preferably 100 mol % or less, and still more preferably 10 mol % or less.

The reaction temperature is not particularly limited, but is preferably 20° C. or more, more preferably 40° C. or more, particularly preferably 70° C. or more, while is preferably 250° C. or less, still more preferably 150° C. or less, and particularly preferably 120° C. or less.

The reaction time is not particularly limited, but is preferably 0.1 hours or more and 100 hours or less.

The catalyst is not particularly limited as long as it is a catalyst enabling a carbonylation reaction of ethylene, and a known catalyst can be used.

Examples thereof include a palladium catalyst having a phosphine-based ligand and the like.

Specific examples of such a catalyst include, for example, a catalyst described in JP-A-10-511034.

Further, such a catalyst can be produced by a known method.

Further, it is preferable that the above reaction is carried out in the presence of an alcohol.

There is no particular limitation on the alcohol, and examples thereof include methanol, ethanol, propanol, 2-propanol, 2-butanol or t-butyl alcohol, and among them, methanol or ethanol is preferred.

Note that 1 kinds of alcohols may be used alone, or 2 or more kinds of alcohols may be used in combination.

The amount of ethylene to alcohol is not particularly limited, but is preferably 0.01 mol % or more, more preferably 0.1 mol % or more, and on the other hand, is preferably 100 mol % or less, and still more preferably 10 mol % or less.

Carbon monoxide may be supplied in combination with an inert gas in the reaction.

Examples of such an inert gas include hydrogen, nitrogen, carbon dioxide, and argon.

Methyl methacrylate can be produced by the method described above, but usually, impurities are contained in the produced methyl methacrylate.

Therefore, in order to remove impurities, it is preferable to purify the obtained methyl methacrylate by a known method such as distillation.

Note that the conditions for purification can be adjusted as necessary to obtain.

EXAMPLES

Hereinafter, the present invention will be described in detail in Examples and Comparative Examples, but the present invention is not limited to the following Examples.

In the following examples, the BET specific surface area of the carrier and the catalyst is a value calculated by BET single point method using a nitrogen adsorption measuring device (trade name: Macsorb, manufactured by Mounted) Co., Ltd.). The number of silanol groups (D (Si—OH)) in the unit area of the carrier and the catalyst was calculated based on the following formula (3) from the value of the weight reduction at 180° C. to 950° C. under the condition of a temperature rise rate of 10° C./min under air flow using a thermogravimetric differential thermal analyzer (manufactured by Rigaku Co., Ltd., model number:TG8120).

$$D(Si\text{—}OH) = 2 \times N_A \times 1/18 \times \Delta wt/100 \times 1/SA \quad \text{formula (3)}$$

$N_A$: Avogadro constant $(6.02 \times 10^{23}\ (\text{mol}^{-1}))$
$\Delta wt$: % weight loss from 180° C. to 950° C.
SA: BET specific surface area $(m^2/g)$.

Further, the molar ratio of the alkali metal element to the first metal element was calculated from the content of the first metal element and the alkali metal element measured by X-ray fluorescence analysis.

In addition, in some examples, a deterioration test of the catalyst was performed.

Specifically, nitrogen was passed through a water saturator heated to 92° C. at a flow rate of 20 ml/min, and further, a tube heated to 385° C. filled with 1 g of catalyst was passed, and the BET specific surface area of the catalyst was measured after 7 days and 28 days of test, and the BET specific surface area reduction rate of the carrier was calculated by the following formula (4).

The examples and comparative examples with catalyst degradation test results in Table 1 are the objects for which the catalyst degradation tests were conducted.

(BET ratio surface area of the catalyst after 28 days of testing-BET ratio surface area of the catalyst after 21 days of testing)/(BET ratio surface area of the catalyst after 7 days of testing)×100    formula (4)

Example 1

4.5 g of zirconium oxynitrate dihydrate (Kishida Chemical, Special Grade) was dissolved in 135 ml of methanol (Nacalai Tesque, Special Grade) and left to stand for 24 hours.

To this solution, 60 g of CARiACT Q-10 (trade name, Fuji Silysia Chemical Co., Ltd., particle size 1.7-4 mm, average pore diameter: 10 nm) used as a carrier was immersed, left to stand for 3.5 hours, and the solvent was evaporated using a rotary evaporator.

Note that the average particle size of zirconium oxynitrate in methanol when the carrier was immersed was 0.8 nm.

Thereafter, drying was performed at 120° C. for 14 hours to obtain a first solid content.

Of the first solid content obtained, 30 g was immersed in a solution in which 4.8 g of cesium carbonate (Wako Pure Chemical Industries, Ltd., Class 1) was dissolved in 65 ml of methanol for 3.5 hours, and the second solid content and the solution were separated by filtration.

The catalyst was obtained by drying the second solid content at 120° C. for 14 hours.

Note that the particle size of the zirconium compound of the catalyst was 0.8 nm to 5 nm.

Next, about 3 g of the catalyst obtained was charged into the reactor.

Thereafter, under normal pressure, a reaction liquid having a molar ratio of methyl propionate, methanol, formaldehyde and water of 11.40:0.19:0.5 was flowed through an evaporator at 300° C. at a liquid feed flow rate of 0.034 ml/min and flowed through a reactor at 330° C. for 16 hours.

Thereafter, under normal pressure, a reaction raw material liquid having a molar ratio of methyl propionate, methanol, formaldehyde and water of 1:0.64:0.27:0.01 was passed through an evaporator at 300° C., and fed into a reactor at 330° C.

The reaction raw material liquid was varied the feed flow rate at five points between 0.034 and 0.35 ml/min, and recovered by cooling and condensing the vapor at the reactor outlet at each feed rate.

The obtained reaction solution was analyzed using gas chromatography (Shimadzu Corporation, trade name: GC-2010), to calculate the yield and selectivity of methacrylic acid and methyl methacrylate at a liquid feed flow rate of 0.16 ml/min by the following formulas (5) and (6), respectively.

The results obtained are shown in Table 1.

(Yield of Methacrylic Acid and Methyl Methacrylate)=(Molar Number of Methacrylic Acid and Methyl Methacrylate Produced)/(Molar Number of Methyl Propionate Supplied)    (formula (5))

(Selectivity of methacrylic acid and methyl methacrylate)=(yield of methacrylic acid and methyl methacrylate)/(conversion ratio of methyl propionate)    formula (6)

Examples 2-7

The selectivity and yield of methacrylic acid and methyl methacrylate were calculated by producing methacrylic acid and methyl methacrylate by the same method as in Example 1, except that a catalyst produced by adjusting the amount of zirconium oxynitrate 2 hydrate and cesium carbonate so that the amount of zirconium and cesium after supporting became the values shown in Table 1.

Note that both of the average particle size of zirconium oxynitrate in methanol when the carrier was immersed were 0.8 nm.

In addition, the particle size of the zirconium compound after catalyst production was 0.8 nm to 5 nm.

The results obtained are shown in Table 1.

Example 8

The selectivity and yield of methacrylic acid and methyl methacrylate were calculated by producing methacrylic acid and methyl methacrylate by the same method as in Example 1, except that the amount of cesium carbonate used was changed to 4.6 g, and a catalyst produced by evaporated the solvent using a rotary evaporator instead of separating the second solid content and the liquid by filtration was used.

Note that the average particle size of zirconium oxynitrate in methanol when the carrier was immersed was 0.8 nm.

In addition, the particle size of the zirconium compound after catalyst production was 0.8 nm to 5 nm.

The results obtained are shown in Table 1.

Examples 9-15

The selectivity and yield of methacrylic acid and methyl methacrylate were calculated by producing methacrylic acid and methyl methacrylate by the same method as in Example 8, except that a catalyst produced by adjusting the amount of zirconium oxynitrate 2 hydrate and cesium carbonate so that the amount of zirconium and cesium after supporting became the values shown in Table 1.

Note that both of the average particle size of zirconium oxynitrate in methanol when the carrier was immersed were 0.8 nm.

In addition, the particle size of the zirconium compound after catalyst production was 0.8 nm to 5 nm.

The results obtained are shown in Table 1.

Example 16

7.3 g of zirconium oxynitrate dihydrate (Kishida Chemical, Special Grade) was dissolved in 57 ml of methanol (Nacalai Tesque, Special Grade) and left to stand for 24 hours.

This solution was impregnated into 60 g of CARiACT Q-10 (trade name, Fuji Silysia Chemical Co., Ltd., particle size 1.7-4 mm, average pore diameter: 10 nm) by a pore filling method.

Note that the average particle size of zirconium oxynitrate in methanol when impregnated into the carrier was 0.8 nm.

Thereafter, drying was performed at 120° C. for 14 hours to obtain a first solid content.

Of the first solid content obtained, a solution obtained by dissolving 7.0 g of cesium carbonate in 29 ml of methanol was impregnated using a pore-filling method with respect to 30 g.

Thereafter, a catalyst was obtained by performing drying for 14 hours at 120° C.

Note that the particle size of the zirconium compound after the catalyst production was 0.8 nm to 5 nm.

Thereafter, methacrylic acid and methyl methacrylate were produced by the same method as in Example 1 to calculate the selectivity and yield of methacrylic acid and methyl methacrylate.

The results obtained are shown in Table 1.

Examples 17-21

Instead of CARiACT Q-10, CARiACT Q15 (trade name, Fuji Silysia Chemical Co., Ltd., particle size: 1.7 mm-4 mm, average pore diameter: 15 nm) was used as a carrier, and further, a catalyst produced by adjusting the amount of zirconium oxynitrate 2 hydrate and cesium carbonate so that the zirconium and cesium amount after supporting became the value shown in Table 1 was used as a carrier, and methacrylic acid and methyl methacrylate were produced by the same method as in Example 1 to calculate the selectivity and yield of methacrylic acid and methyl methacrylate.

Note that both of the average particle size of zirconium oxynitrate in methanol when the carrier was immersed were 0.8 nm.

In addition, the particle size of the zirconium compound after catalyst production was 0.8 nm to 5 nm.

The results obtained are shown in Table 1.

Examples 22-27

Instead of CARiACT Q-10, CARiACT Q15C (trade name, Fuji Silysia Chemical Co., Ltd., particle size: 1.7 mm-4 mm, average pore diameter: 15 nm) was used as a carrier, and further, a catalyst produced by adjusting the amount of zirconium oxynitrate 2 hydrate and cesium carbonate so that the zirconium and cesium amount after supporting became the value shown in Table 1 was used as a carrier, and methacrylic acid and methyl methacrylate were produced by the same method as in Example 1 to calculate the selectivity and yield of methacrylic acid and methyl methacrylate.

Note that both of the average particle size of zirconium oxynitrate in methanol when the carrier was immersed were 0.8 nm.

In addition, the particle size of the zirconium compound after catalyst production was 0.8 nm to 5 nm.

The results obtained are shown in Table 1.

Examples 28-32

Instead of CARiACT Q-10, CARiACT Q30 (trade name, Fuji Silysia Chemical Co., Ltd., particle size: 1.7 mm-4 mm, average pore diameter: 30 nm) was used as a carrier, and, a catalyst produced by adjusting the amount of zirconium oxynitrate 2 hydrate and cesium carbonate so that the zirconium and cesium amount after supporting became the value shown in Table 1 was used as a carrier, and methacrylic acid and methyl methacrylate were produced by the same method as in Example 1 to calculate the selectivity and yield of methacrylic acid and methyl methacrylate.

Note that both of the average particle size of zirconium oxynitrate in methanol when the carrier was immersed were 0.8 nm.

In addition, the particle size of the zirconium compound after catalyst production was 0.8 nm to 5 nm.

The results obtained are shown in Table 1.

Examples 33-39

Instead of CARiACT Q-10, CARiACT Q30C (trade name, Fuji Silysia Chemical Co., Ltd., particle size: 1.7 mm-4 mm, average pore diameter: 30 nm) was used as a carrier, and, a catalyst produced by adjusting the amount of zirconium oxynitrate 2 hydrate and cesium carbonate so that the zirconium and cesium amount after supporting became the value shown in Table 1 was used as a carrier, and methacrylic acid and methyl methacrylate were produced by the same method as in Example 1 to calculate the selectivity and yield of methacrylic acid and methyl methacrylate.

Note that both of the average particle size of zirconium oxynitrate in methanol when the carrier was immersed were 0.8 nm.

In addition, the particle size of the zirconium compound after catalyst production was 0.8 nm to 5 nm.

The results obtained are shown in Table 1.

Comparative Example 1

The selectivity and yield of methacrylic acid and methyl methacrylate were calculated by producing methacrylic acid and methyl methacrylate by the same method as in Example 1, except that a catalyst produced by adjusting the amount of zirconium oxynitrate 2 hydrate and cesium carbonate so that the amount of zirconium and cesium after supporting became the values shown in Table 1.

Note that both of the average particle size of zirconium oxynitrate in methanol when the carrier was immersed were 0.8 nm.

In addition, the particle size of the zirconium compound after catalyst production was 0.8 nm to 5 nm.

The results obtained are shown in Table 1.

Comparative Example 2

The selectivity and yield of methacrylic acid and methyl methacrylate were calculated by producing methacrylic acid and methyl methacrylate by the same method as in Example 26, except that a catalyst produced by adjusting the amount of zirconium oxynitrate 2 hydrate and cesium carbonate so that the amount of zirconium and cesium after supporting became the values shown in Table 1.

Note that both of the average particle size of zirconium oxynitrate in methanol when the carrier was immersed were 0.8 nm.

In addition, the particle size of the zirconium compound after catalyst production was 0.8 nm to 5 nm.

The results obtained are shown in Table 1.

Comparative Example 3

The selectivity and yield of methacrylic acid and methyl methacrylate were calculated by producing methacrylic acid and methyl methacrylate by the same method as in Example 39, except that a catalyst produced by adjusting the amount of zirconium oxynitrate 2 hydrate and cesium carbonate so that the amount of zirconium and cesium after supporting became the values shown in Table 1.

Note that both of the average particle size of zirconium oxynitrate in methanol when the carrier was immersed were 0.8 nm.

In addition, the particle size of the zirconium compound after catalyst production was 0.8 nm to 5 nm.

The results obtained are shown in Table 1.

Example 40

5.4 g of zirconium oxynitrate dihydrate (Kishida Chemical, Special Grade) was dissolved in 125 ml of methanol (Nacalai Tesque, Special Grade) and left to stand for 24 hours.

This solution was impregnated into 130 g of CARiACT Q-10 (trade name, Fuji Silysia Chemical Co., Ltd., particle size 1.7-4 mm, average pore diameter: 10 nm) by a pore filling method.

Note that the average particle size of zirconium oxynitrate in methanol when impregnated into the carrier was 0.8 nm.

Thereafter, drying was performed at 120° C. for 14 hours to obtain a first solid content.

Of the first solid content obtained, a solution obtained by dissolving 1.9 g of cesium carbonate (Wako Pure Chemical Industries, 1st class) in 29 ml of methanol was impregnated using a pore-filling method with respect to 30 g.

Thereafter, after performing drying for 14 hours at 120° C., a catalyst was obtained by performing calcination for 3 hours at 600° C.

Note that the particle size of the zirconium compound after the catalyst production was 0.8 nm to 5 nm.

Next, about 3 g of the catalyst obtained was charged into the reactor

Thereafter, under normal pressure, a reaction liquid having a molar ratio of methyl propionate, methanol, formaldehyde and water of 1:1.40:0.19:0.5 was flowed through an evaporator at 300° C. at a liquid feed flow rate of 0.034 ml/min and flowed through a reactor at 350° C. for 16 hours.

Thereafter, under normal pressure, a reaction raw material liquid having a molar ratio of methyl propionate, methanol, formaldehyde and water of 1:1.40:0.19:0.5 was passed through an evaporator at 300° C., and fed into a reactor at 350° C.

The reaction raw material liquid was varied the feed flow rate at five points between 0.35 and 0.034 ml/min, and recovered by cooling and condensing the vapor at the reactor outlet at each feed rate.

The obtained reaction solution was analyzed using gas chromatography (Shimadzu Corporation, trade name: GC-2010) to calculate the yield and selectivity of methacrylic acid and methyl methacrylate at a liquid feed flow rate of 0.16 ml/min, respectively.

The results obtained are shown in Table 1

Examples 41-42

The selectivity and yield of methacrylic acid and methyl methacrylate were calculated by producing methacrylic acid and methyl methacrylate by the same method as in Example 40, except that a catalyst produced by adjusting the amount of zirconium oxynitrate 2 hydrate and cesium carbonate so that the amount of zirconium and cesium after supporting became the values shown in Table 1

Note that both of the average particle size of zirconium oxynitrate in methanol when the carrier was immersed were 0.8 nm.

In addition, the particle size of the zirconium compound after catalyst production was 0.8 nm to 5 nm.

The results obtained are shown in Table 1.

Examples 43-45

Instead of methanol, water was used as the solvent, and further, a catalyst produced by adjusting the amount of zirconium oxynitrate 2 hydrate and cesium carbonate so that the zirconium and cesium amount after supporting became the value shown in Table 1 was used as a carrier, and methacrylic acid and methyl methacrylate were produced by the same method as in Example 40 to calculate the selectivity and yield of methacrylic acid and methyl methacrylate.

Note that both of the average particle size of zirconium oxynitrate in methanol when the carrier was immersed were 0.8 nm.

In addition, the particle size of the zirconium compound after catalyst production was 0.8 nm to 5 nm.

The results obtained are shown in Table

Examples 46-49

The time to left zirconium oxynitrate to stand in methanol was changed from 24 hours to 15 minutes, and further, a catalyst produced by adjusting the amount of zirconium oxynitrate 2 hydrate and cesium carbonate so that the zirconium and cesium amount after supporting became the value shown in Table 1 was used as a carrier, and methacrylic acid and methyl methacrylate were produced by the same method as in Example 42 to calculate the selectivity and yield of methacrylic acid and methyl methacrylate.

Note that both of the average particle size of zirconium oxynitrate in methanol when the carrier was immersed were 10 to 50 nm.

The results obtained are shown in Table 1.

TABLE 1

| | Carrier | | Catalyst Component | | | | | MMA + MAA yield (%) | MMA + MAA selectivity (%) | BET specific surface area reduction rate (%) |
|---|---|---|---|---|---|---|---|---|---|---|
| | BET specific surface area (m²/g) | Number of Si-OH groups Z' (number/nm²) | Cs (wt %) | Zr (wt %) | Cs/Zr molar ratio X | X/(Y × Z) (×10⁻²¹ g/number) | X'/(Y' × Z') (×10⁻²¹ g/number) | | | |
| Ex.1 | 312 | 0.8 | 8.5 | 2.1 | 2.8 | 7.0 | 11.2 | 12.4 | 97.2 | 7.68 |
| Ex.2 | 312 | 0.8 | 10.1 | 2.1 | 3.3 | 8.2 | 13.2 | 13.8 | 96.1 | 7.05 |
| Ex.3 | 312 | 0.8 | 11.4 | 2.1 | 3.7 | 9.2 | 14.9 | 14.3 | 95.4 | 7.69 |
| Ex.4 | 312 | 0.8 | 7.8 | 3.1 | 1.7 | 4.3 | 6.9 | 13.8 | 95.9 | 9.16 |
| Ex.5 | 312 | 0.8 | 10.4 | 3.3 | 2.2 | 5.5 | 8.8 | 15.0 | 95.0 | 4.20 |
| Ex.6 | 312 | 0.8 | 10.9 | 4.7 | 1.6 | 4.0 | 6.4 | 14.5 | 95.9 | — |
| Ex.7 | 312 | 0.8 | 13.0 | 4.7 | 1.9 | 4.7 | 7.5 | 15.1 | 94.0 | — |
| Ex.8 | 312 | 0.8 | 8.3 | 2.2 | 2.5 | 6.3 | 10.2 | 17.3 | 96.2 | — |
| Ex.9 | 312 | 0.8 | 8.6 | 2.1 | 2.8 | 7.0 | 11.2 | 13.5 | 96.9 | 4.86 |
| Ex.10 | 312 | 0.8 | 10.8 | 2.1 | 3.6 | 9.0 | 14.4 | 14.2 | 95.7 | — |
| Ex.11 | 312 | 0.8 | 12.4 | 2.1 | 4.0 | 10.0 | 16.2 | 12.6 | 94.1 | 11.96 |
| Ex.12 | 312 | 0.8 | 9.0 | 3.4 | 1.8 | 4.6 | 7.3 | 14.1 | 96.0 | 11.41 |
| Ex.13 | 312 | 0.8 | 10.6 | 3.3 | 2.2 | 5.6 | 9.0 | 14.4 | 95.5 | — |
| Ex.14 | 312 | 0.8 | 12.1 | 3.2 | 2.6 | 6.4 | 10.3 | 15.2 | 94.8 | 6.75 |
| Ex.15 | 312 | 0.8 | 14.9 | 3.4 | 3.0 | 7.5 | 12.0 | 9.5 | 94.8 | — |
| Ex.16 | 312 | 0.8 | 12.7 | 3.4 | 2.6 | 6.4 | 10.2 | 13.9 | 94.8 | — |
| Ex.17 | 199 | 4 | 8.6 | 2.1 | 2.7 | 2.1 | 3.4 | 15.7 | 94.8 | — |
| Ex.18 | 199 | 4 | 10.4 | 2.4 | 3.0 | 2.4 | 3.8 | 16.5 | 94.7 | — |
| Ex.19 | 199 | 4 | 10.8 | 2.2 | 3.5 | 2.7 | 4.3 | 16.4 | 94.2 | 5.39 |
| Ex.20 | 199 | 4 | 9.7 | 3.5 | 1.9 | 1.5 | 2.4 | 15.1 | 94.8 | 1.11 |
| Ex.21 | 199 | 4 | 12.0 | 3.7 | 2.2 | 1.7 | 2.8 | 16.6 | 94.0 | 2.49 |
| Ex.22 | 186 | 6.4 | 7.0 | 2.1 | 2.2 | 1.2 | 1.9 | 10.3 | 95.4 | — |
| Ex.23 | 186 | 6.4 | 8.6 | 2.3 | 2.6 | 1.3 | 2.2 | 11.7 | 96.0 | — |
| Ex.24 | 186 | 6.4 | 9.7 | 2.3 | 3.0 | 1.5 | 2.5 | 13.2 | 95.3 | — |
| Ex.25 | 186 | 6.4 | 10.8 | 2.3 | 3.3 | 1.7 | 2.8 | 13.4 | 95.4 | 5.04 |
| Ex.26 | 186 | 6.4 | 12.2 | 2.2 | 3.8 | 2.0 | 3.2 | 13.1 | 94.3 | — |
| Ex.27 | 186 | 6.4 | 12.8 | 3.4 | 2.6 | 1.4 | 2.2 | 15.2 | 94.8 | 4.96 |
| Ex.28 | 117 | 5.8 | 5.9 | 1.0 | 4.0 | 3.6 | 5.8 | 11.0 | 96.0 | — |
| Ex.29 | 117 | 5.8 | 7.3 | 1.1 | 4.6 | 4.2 | 6.7 | 11.8 | 96.0 | — |
| Ex.30 | 117 | 5.8 | 8.2 | 1.1 | 5.2 | 4.7 | 7.6 | 12.7 | 95.6 | 6.81 |
| Ex.31 | 117 | 5.8 | 6.8 | 2.3 | 2.0 | 1.8 | 2.9 | 12.9 | 94.4 | — |
| Ex.32 | 117 | 5.8 | 7.8 | 2.2 | 2.5 | 2.3 | 3.6 | 13.7 | 94.4 | — |
| Ex.33 | 94 | 10.2 | 4.9 | 1.1 | 3.1 | 2.0 | 3.3 | 12.4 | 96.0 | — |
| Ex.34 | 94 | 10.2 | 6.1 | 1.0 | 4.1 | 2.7 | 4.3 | 13.8 | 96.1 | — |
| Ex.35 | 94 | 10.2 | 7.9 | 1.1 | 4.9 | 3.2 | 5.1 | 13.9 | 95.7 | — |
| Ex.36 | 94 | 10.2 | 8.6 | 1.1 | 5.6 | 3.6 | 5.8 | 14.2 | 94.8 | 1.93 |
| Ex.37 | 94 | 10.2 | 6.4 | 2.2 | 2.0 | 1.3 | 2.1 | 10.4 | 94.2 | — |
| Ex.38 | 94 | 10.2 | 7.7 | 2.2 | 2.4 | 1.6 | 2.5 | 11.7 | 94.8 | — |
| Ex.39 | 94 | 10.2 | 9.9 | 2.2 | 3.1 | 2.0 | 3.2 | 10.9 | 94.0 | — |
| Comp.Ex.1 | 312 | 0.8 | 14.5 | 2.3 | 4.4 | 11.0 | 17.6 | 10.4 | 93.1 | — |
| Comp.Ex2 | 199 | 4 | 5.9 | 3.6 | 1.1 | 0.9 | 1.4 | 2.5 | 25.4 | — |
| Comp.Ex3 | 186 | 6.4 | 7.3 | 3.2 | 1.6 | 0.8 | 1.3 | 6.6 | 63.6 | — |
| Ex.40 | 312 | 0.8 | 4.8 | 1.2 | 2.6 | 6.6 | 10.6 | 8.0 | 97.4 | 15.76 |
| Ex.41 | 312 | 0.8 | 5.8 | 1.3 | 3.0 | 7.4 | 11.9 | 9.7 | 96.0 | 15.27 |
| Ex.42 | 312 | 0.8 | 6.4 | 1.2 | 3.7 | 9.2 | 14.9 | 9.5 | 95.9 | 14.96 |
| Ex.43 | 312 | 0.8 | 4.8 | 1.3 | 2.6 | 6.5 | 10.4 | 8.2 | 97.6 | 9.76 |
| Ex.44 | 312 | 0.8 | 5.5 | 1.2 | 3.2 | 8.0 | 12.8 | 9.7 | 96.6 | — |
| Ex.45 | 312 | 0.8 | 6.7 | 1.3 | 3.6 | 9.0 | 14.4 | 10.5 | 96.2 | 10.37 |
| Ex.46 | 312 | 0.8 | 4.3 | 1.4 | 2.1 | 5.1 | 8.3 | 7.4 | 97.1 | 19.51 |
| Ex.47 | 312 | 0.8 | 5.0 | 1.3 | 2.6 | 6.4 | 10.2 | 8.7 | 97.0 | 17.85 |
| Ex.48 | 312 | 0.8 | 6.2 | 1.4 | 3.1 | 7.7 | 12.3 | 8.9 | 96.7 | 23.01 |
| Ex.49 | 312 | 0.8 | 7.2 | 1.3 | 3.8 | 9.5 | 15.3 | 8.9 | 96.7 | 19.18 |

In Table 1, Cs (wt %) represents the content of cesium relative to the total mass of the catalyst component and the carrier, Zr (wt %) represents the content of zirconium relative to the total mass of the catalyst component and the carrier, and Cs/Zr molar ratio X represents the molar ratio of cesium to zirconia in the catalyst component.

In addition, the MMA+MAA yield (%) and the MMA+MAA selectivity (%) represent the yield and selectivity of methyl methacrylate and methacrylic acid, respectively.

As can be seen from the results of Table 1, it can be seen that, compared to Comparative Examples 1 to 3 using a catalyst which does not satisfy the above formula (1), the selectivity of methacrylic acid and methyl methacrylate is greatly improved by using a catalyst satisfying the above formula (1)

The invention claimed is:
1. A method for producing an unsaturated carboxylic acid by reacting a carboxylic acid with formaldehyde in the presence of a catalyst,
  wherein the catalyst comprises:
  (i) a compound comprising at least one first element selected from boron, magnesium, zirconium, and hafnium; and

(ii) an alkali metal element,
wherein the compound and the alkali metal element are supported on a carrier having silanol groups,
an average particle size of the compound is 0.4 nm or more and 50 nm or less, and
the catalyst satisfies the following formula (1):

$$0.90 \times 10^{-21} \text{(g/number)} \leq X/(Y \times Z) < 10.8 \times 10^{-21} \text{(g/number)} \quad \text{formula (1),}$$

in which X is a molar ratio of the alkali metal element to the at least one first element in the catalyst, Y is a BET specific surface area of the catalyst ($m^2/g$), and Z is a number of the silanol groups per unit area (number/$nm^2$).

2. The method according to claim 1, wherein X is 1.3 or more and 6.0 or less.

3. The method according to claim 1, wherein the alkali metal element comprises cesium.

4. The method according to claim 1, wherein the at least one first element comprises zirconium.

5. The method according to claim 1, wherein the catalyst is produced by a method for producing a catalyst comprises (i) a compound comprising at least one first element selected from boron, magnesium, zirconium, and hafnium; and (ii) an alkali metal element, the compound and the alkali metal element being supported on a carrier having silanol groups, the method comprising
impregnating the carrier with a solution or dispersion containing an inorganic salt of the at least one first element to obtain a first solid, and
impregnating the first solid with a solution or dispersion containing the alkali metal salt to obtain the second solid,
wherein an average particle size of the compound is 0.4 nm or more and 50 nm or less, and
the catalyst satisfies the following formula (2):

$$1.5 \times 10^{-21} \text{(g/number)} \leq X'/(Y' \times Z') \leq 17.0 \times 10^{-21} \text{(g/number)} \quad \text{formula (1),}$$

in which X' is a molar ratio of the alkali metal element to the at least one first element in the catalyst, Y' is a BET specific surface area of the catalyst ($m^2/g$), and Z' is a number of the silanol groups per unit area (number/$nm^2$).

6. The method according to claim 5, wherein the solution or dispersion containing the inorganic salt of the at least one first element contains alcohol.

7. The method according to claim 5, wherein the at least one first element comprises zirconium.

8. The method according to claim 5, wherein the alkali metal element comprises cesium.

9. The method according to claim 5, wherein the at least one first element comprises boron.

10. The method according to claim 5, wherein the at least one first element comprises magnesium.

11. The method according to claim 5, wherein the at least one first element comprises zirconium.

12. The method according to claim 5, wherein the at least one first element comprises hafnium.

13. The method according to claim 1, wherein the at least one first element comprises boron.

14. The method according to claim 1, wherein the at least one first element comprises magnesium.

15. The method according to claim 1, wherein the at least one first element comprises hafnium.

16. A method for producing an unsaturated carboxylic acid ester by reacting a carboxylic acid with formaldehyde in the presence of a catalyst
wherein the catalyst comprises:
(i) a compound comprising at least one first element selected from boron, magnesium, zirconium, and hafnium; and
(ii) an alkali metal element,
wherein the compound and the alkali metal element are supported on a carrier having silanol groups,
an average particle size of the compound is 0.4 nm or more and 50 nm or less, and
the catalyst satisfies the following formula (1):

$$0.90 \times 10^{-21} \text{(g/number)} \leq X/(Y \times Z) < 10.8 \times 10^{-21} \text{(g/number)} \quad \text{formula (1),}$$

in which X is a molar ratio of the alkali metal element to the at least one first element in the catalyst, Y is a BET specific surface area of the catalyst ($m^2/g$), and Z is a number of the silanol groups per unit area (number/$nm^2$).

17. The method according to claim 16, wherein X is 1.3 or more and 6.0 or less.

18. The method according to claim 16, wherein the alkali metal element comprises cesium.

19. The method according to claim 16, wherein the at least one first element comprises zirconium.

* * * * *